United States Patent
Pelz et al.

(10) Patent No.: US 12,208,025 B2
(45) Date of Patent: Jan. 28, 2025

(54) UNIBODY ENDOSKELETAL TRANSTIBIAL PROSTHETIC DEVICES AND DIGITAL FABRICATION WORKFLOW

(71) Applicant: The Regents of The University of California, Oakland, CA (US)

(72) Inventors: Joshua Pelz, San Diego, CA (US); Luca De Vivo, San Diego, CA (US); Falko Kuester, La Jolla, CA (US); Herbert J. Barrack, San Diego, CA (US)

(73) Assignee: The Regents of The University of California, Oakland, CA (US)

( * ) Notice: Subject to any disclaimer, the term of this patent is extended or adjusted under 35 U.S.C. 154(b) by 0 days.

(21) Appl. No.: 18/581,180

(22) Filed: Feb. 19, 2024

(65) Prior Publication Data
US 2024/0189118 A1    Jun. 13, 2024

Related U.S. Application Data

(63) Continuation of application No. 18/009,915, filed as application No. PCT/US2022/011939 on Jan. 11, 2022.
(Continued)

(51) Int. Cl.
*A61F 2/60* (2006.01)
*A61F 2/50* (2006.01)
(Continued)

(52) U.S. Cl.
CPC .............. *A61F 2/60* (2013.01); *A61F 2/5046* (2013.01); *A61F 2/6607* (2013.01); *A61F 2/80* (2013.01);
(Continued)

(58) Field of Classification Search
CPC ........ A61F 2/60; A61F 2/5046; A61F 2/6607; A61F 2/80; A61F 2002/505;
(Continued)

(56) References Cited

U.S. PATENT DOCUMENTS

| 4,959,073 A | 9/1990 | Merlette |
| 5,181,933 A | 1/1993 | Phillips |

(Continued)

FOREIGN PATENT DOCUMENTS

| DE | 202018102687 U1 | 9/2019 |
| EP | 2803337 B1 | 1/2019 |

(Continued)

OTHER PUBLICATIONS

Ashworth. Pet prosthetics get a boost from 3D printing. (Year: 2020).
(Continued)

*Primary Examiner* — Neil R McLean
(74) *Attorney, Agent, or Firm* — MLO, a professional corp.

(57) ABSTRACT

A transtibial prosthetic device comprises a pylon configured as a unitary truss structure formed of a plurality of elongated supports interconnected at nodes and having open spaces between supports of the plurality of elongated supports. The unitary truss structure comprises a polymer. A foot-ankle complex extends from a base of the pylon. The foot-ankle complex comprises an s-shaped posterior portion, an s-shaped anterior portion, and a sole portion. The s-shaped posterior portion and the s-shaped anterior portion both extend from the sole portion, have upper portions with curvatures that are concentric with each other, and are separated from each other by a gap.

20 Claims, 8 Drawing Sheets

Related U.S. Application Data

(60) Provisional application No. 63/137,268, filed on Jan. 14, 2021.

(51) Int. Cl.
*A61F 2/66* (2006.01)
*A61F 2/80* (2006.01)
*B33Y 50/00* (2015.01)
*B33Y 80/00* (2015.01)

(52) U.S. Cl.
CPC ............... *B33Y 50/00* (2014.12); *B33Y 80/00* (2014.12); *A61F 2002/505* (2013.01); *A61F 2002/607* (2013.01); *A61F 2002/6621* (2013.01); *A61F 2002/6642* (2013.01); *A61F 2002/6685* (2013.01)

(58) Field of Classification Search
CPC ........ A61F 2002/607; A61F 2002/6621; A61F 2002/6642; A61F 2002/6685; A61F 2002/6664; A61F 2002/785; B33Y 50/00; B33Y 80/00; B33Y 10/00; B29C 64/118
USPC .......................................................... 623/33
See application file for complete search history.

(56) References Cited

U.S. PATENT DOCUMENTS

| | | | |
|---|---|---|---|
| 5,509,936 A | 4/1996 | Rappoport et al. | |
| 5,545,234 A | 8/1996 | Collier, Jr. | |
| 5,653,768 A | 8/1997 | Kania | |
| 7,347,877 B2 | 3/2008 | Clausen et al. | |
| 8,025,699 B2 | 9/2011 | Lecomte et al. | |
| 8,366,789 B2 | 2/2013 | Summit | |
| 9,078,773 B2 | 7/2015 | Zamora et al. | |
| 9,439,767 B2 * | 9/2016 | Bojarski | A61F 2/30 |
| 9,480,581 B2 | 11/2016 | Layman et al. | |
| 10,010,433 B2 | 7/2018 | Layman et al. | |
| 2003/0009238 A1 | 1/2003 | Whayne | |
| 2011/0004335 A1 | 1/2011 | Summit et al. | |
| 2011/0107581 A1 | 5/2011 | Williams et al. | |
| 2013/0150981 A1 * | 6/2013 | Summit | A61F 2/60 623/33 |
| 2013/0267878 A1 | 10/2013 | Franke et al. | |
| 2017/0360578 A1 | 12/2017 | Shin et al. | |
| 2020/0276030 A1 | 9/2020 | LaBelle et al. | |

FOREIGN PATENT DOCUMENTS

| | | |
|---|---|---|
| FR | 2384488 A1 | 10/1977 |
| JP | 2003144484 A | 5/2003 |
| JP | 2017000388 A | 1/2017 |

OTHER PUBLICATIONS

Birrell. 3D Printed Prosthetic Limbs: The next revolution in medicine. (Year: 2017).
Hemsworth. Hiking enabled prosthetic legs. (Year: 2017).
International Search Report from the corresponding International Patent Application No. PCT/US22/11939, dated Jul. 19, 2022.
Junkie, Gadget. Lytra prosthetic leg for shower. (Year: 2007).
Notice of Allowance and Fees dated Nov. 29, 2023 for U.S. Appl. No. 18/009,915.
Office Action dated Dec. 28, 2023 for U.S. Appl. No. 18/185,011.
Office Action dated Jul. 12, 2023 for U.S. Appl. No. 18/185,011.
Office Action dated Sep. 21, 2023 for U.S. Appl. No. 18/185,011.
Ottobock, Ottobock Prosthetic Foot Solutions Web Page, Prosthetic Foot Solutions: Mechanical Feet, dowloaded Dec. 14, 2021.
Translation of DE202018102687U1 (Year: 2020).
Translation of FR2384488A1 (Year: 1977).
Valenti, Thomas G., "Experience with Endoflex: A Monolithic Thermoplastic Prosthesis for Below-Knee Amputees", Journal of Prosthetics and Orthotics, 1990, vol. 3, No. 1, pp. 43-50.
Yusuf. This is the first 3D printed prosthetic limb in the UAE. (Year: 2017).
European Search Report dated Oct. 31, 2024 for European Patent Office Patent Application No. 22750148.3.

* cited by examiner

UNIBODY ENDOSKELETAL TRANSTIBIAL PROSTHETIC DEVICES AND DIGITAL FABRICATION WORKFLOW

PRIORITY CLAIM AND REFERENCE TO RELATED APPLICATION

This application is a continuation of and claims priority under 35 U.S.C. § 120 from prior pending U.S. application Ser. No. 18/009,915, which was filed on Dec. 12, 2022, which was a U.S. National Phase under 35 U.S.C. § 371 of International Application No. PCT/US2022/011939, filed Jan. 11, 2022, which is incorporated by reference herein and which claims priority under 35 U.S.C. § 119 and all applicable statutes and treaties from prior U.S. provisional application Ser. No. 63/137,268 which was filed Jan. 14, 2021.

STATEMENT OF GOVERNMENT INTEREST

This invention was made with government support under grant number CNS-1338192 awarded by the National Science Foundation, under grant number 70NANB17H211 awarded by the National Institute of Standards and Technology, and under grant number W912HZ172-0024 awarded by the US Army Research Office. The government has certain rights in the invention.

FIELD

A field of the invention is transtibial prosthetic devices.

BACKGROUND

In 2017, the World Health Organization (WHO) estimated that globally there were 35-40 million people in need of prosthetics or other assistive devices, with this number expected to double by 2050. Only 5-15% of people in need have access to prosthetics or other assistive devices, in both underserved and developed countries. As a result, a staggering 34-38 million people, 2.1 million of whom are in the United States, live restricted and often painful lives. Among the contributing medical conditions that are causing more than 185,000 Americans to lose limbs every year are vascular disease (54%), trauma (44%), and cancer (2%). People with diabetes are especially prone to vascular problems necessitating lower limb amputation and this situation has been exacerbated by the COVID-19 pandemic. The elderly, particularly in aging populations with an increased incidence of diabetes, are especially at risk. Mobility and health-related issues resulting from amputation adversely affect patients' quality of life and, particularly in children and adolescents, may result in psychological and psychosocial issues as well. Recovery and rehabilitation are adversely affected by the cost and manufacturing time of prosthetics. This situation is particularly serious in developing countries where amputees often have limited access to medical facilities and experienced practitioners.

Conventional transtibial prosthetic devices are formed from multiple expensive components. Patient specific designs are typically achieved by manual molding, sculpting and composite lay-up to fabricate the socket, and then assembling an appropriate prosthetic from expensive $3^{rd}$-party components.

The three basic components of a conventional transtibial prosthetic limb include the socket, pylon, and ankle-foot complex. The socket attaches the prosthesis to the wearer, such as via corsets, straps, lock-pins, or vacuums. Sockets are typically made from composite materials such as Carbon Fiber Reinforced Polymer (CFRP). The pylon is commonly made of CFRP or aluminum and is used to adjust height and transfer load between the socket and foot. Connections between socket, pylon, and ankle-foot complex can be made with pyramid connectors, which allow for proper trochanter (hip)-knee-ankle (TKA) line adjustment. Adjustable prosthetic devices are called endoskeletal systems and are very popular for a number of reasons, including greater flexibility, lower weight, improved gait performance and better comfort, among other things. If components are rigidly fixed together and cannot be aligned post-fabrication, the device is an exoskeletal system. The ankle-foot complex serves to interface with the ground and can be active or passive to provide proper gait mobility. Simpler passive systems are stiff and don't enable energy capture and release, which results in high metabolic cost for walking and an asymmetrical gait. High-performance passive systems use special materials and designs to store and release energy during the gait cycle to reduce metabolic cost of walking and increase comfort and functionality. Active systems use powered motors, servos, and sensors to control the gait cycle and can significantly enhance performance. However, active systems are prohibitively expensive, less reliable, require a power-source, and very difficult to access for the majority of the world's amputee population.

The fitting process for a conventional prosthetic device is complex and expensive, requiring multiple steps. Prosthetists require many years, if not decades, of experience to be able to provide effective prosthetic care using traditional molding and sculpting processes. One of the main reasons amputees choose not to wear their device is an uncomfortable socket, and the socket will only be as good as the prosthetist who shapes it. Further, to solve the prosthetic accessibility crisis, it is estimated upwards of 75,000 more prosthetists are needed worldwide; training new prosthetists is an expensive time-consuming endeavor.

Designs of the ankle-foot complex have benefited from advancements in materials science and manufacturing technology. In general, whether the foot-ankle complex is active or passive, the top of the complex includes a horizontal edge to offer a connection with the pylon. The Solid Ankle Cushioned Heel (SACH) model is a simple passive prosthetic foot having a resilient foot inset. The static design of the SACH foot, results in asymmetric gait characteristics, high metabolic costs, and low energy return benefit.

While basic prosthetic foot models similar to the SACH model are commonly used, new materials and designs are emerging. New models include running-blades, the Niagara foot and the Seattle foot, among others. Running-blades are carbon fiber blade-type feet that are designed for running, but suffer in walking situations. The Niagara foot, a futuristic-looking solid ankle foot, is made from Hytrel. Hytrel is a thermoplastic polyester elastomer that provides superior durability and energy return. The Niagara foot has been tested to more than 3,000,000 loading-cycles and shows increased durability over carbon fiber feet. "Niagara-foot," [Online] http://protosthetics.com/niagara-foot. Seattle feet incorporate molded and manufactured components of various materials including carbon fiber, nylon, and metal. Seattle feet can either be bolted directly to the pylon or attached with special adapters that simulate ankle articulation. Feet prosthetics: Prosthetic products: Global. [Online] https://trulife.com/product-category/prosthetics/feet/.

More recent efforts focus on digital fabrication and additive manufacturing. Summit U.S. Pat. No. 8,366,789 describes a method to create an exoskeletal prosthetic limb that can be simultaneously printed in one piece from a single material. Although the designs disclosed in this patent are novel, exoskeletal systems have lost favor over endoskeletal systems due to many limiting factors. One such important factor is the inability to adjust the design post-fabrication, which is a common problem for all amputees and even more important for new amputees whose amputated limb will change shape significantly during the first several months to 1 year. If exoskeletal devices are used for these newer amputees, the patient will either endure a painful, poorly functioning socket or must go back to the prosthetist to be remeasured and a new device constructed. One disclosed design includes elongated members that span the length of the lower leg having front and rear members that resemble the outer shape of the contralateral limb. Weight is distributed between the front and rear members. These members are coupled with a basic solid foot and are printed in a single photopolymer material. The use of a single material has significant disadvantages in functionality, because regions that would benefit from being stiff have to compromise with regions that should be flexible and compliant. Further, while the vat photopolymerization method, specified by Summit as the preferred printer type, can produce detailed parts with fine features, photopolymers generally have lower strength, flexibility, and durability compared to thermopolymers. Other disclosed designs include ball and socket connections between an elongated front member to the foot. Other designs include multiple mechanical linkages in the knee area and ball and sockets in the ankle area. The mechanical linkage and ball and socket connections are likely to wear and become loose after many cycles of movement, which will negatively affect the gait of a user. The simple foot and solid elongate supports that extend from knee to foot will be relatively thick and heavy to meet requirement for applied forces. The use of photopolymer material will lead to catastrophic failure if loads exceed material capability, and could result in a severely injured patient.

Layman et al. U.S. Pat. No. 10,010,433 and Layman et al. U.S. Pat. No. 9,480,581 describes imaging and digital processes to make a 3-D printed socket. A check socket is first fabricated and matched with traditional alignment connectors, pylon, and foot/ankle componentry. Alignment and socket fit adjustment is achieved through manual methods requiring an experienced prosthetist and patient visits. A digital copy of the aligned device is then produced using a scanner. The digital copy is used to design a patient-fit socket with attachment points aligned for the specific patient. The printed socket may improve fit, but the time-consuming and manual fitting and alignment process will reduce the efficacy of this method. Further, the use of traditional hardware, connectors, pylon, and ankle-foot complex will increase cost and weight, while reducing time savings and customization afforded by a digital process.

Valenti, "Experience with Endoflex: A Monolithic Thermoplastic Prosthesis for Below-Knee Amputees," Journal of Prosthetics and Orthotics, Volume 3, Number 1, pp. 43-50 describes monolithic socket and rod-shaped solid pylon that can be fitted to a prosthetic foot.

The creation and fitting of prosthetic devices remains expensive. Most patients are fitted with prosthetic devices that are formed from separate and expensive components. Separate components add weight, complexity, and expense.

Recently, a Japanese company Instalimb has used 3D-CAD, 3D printing and machine learning (AI) technology to create a 3D printed transtibial prosthetic. The printed prosthesis is a printed socket parts that is then joined with a standard solid pylon and foot. The printed socket offers a cost and fitting advantage compared prior devices. Fitting of a pylon and foot still requires skill and can be expensive.

SUMMARY OF THE INVENTION

A preferred embodiment provides a unibody transtibial prosthetic device that includes a socket configured to attach to a residual limb. A pylon extends from the socket, the pylon being a unitary polymer structure of interconnected elongated supports having open spaces therebetween. The device also includes a foot-ankle complex, the foot-ankle complex being a unitary polymer extending from the pylon, the foot and ankle unitary structure being shaped to provide multi-axial dynamic flex.

An embodiment provides a transtibial prosthetic device comprising a pylon configured as a unitary truss structure formed of a plurality of elongated supports interconnected at nodes and having open spaces between supports of the plurality of elongated supports. The unitary truss structure comprises a polymer. A foot-ankle complex extends from a base of the pylon. The foot-ankle complex comprises a sole portion; an s-shaped posterior portion extending from a first location on the sole portion to the base of the pylon; and an s-shaped anterior portion extending from a second location on the sole portion to a terminal portion of the s-shaped anterior portion near the base of the pylon. The terminal portion is unconnected to the base of the pylon. The s-shaped posterior portion and the s-shaped anterior portion are separated from each other by a gap that extends from the terminal portion to the sole portion.

An embodiment provides a transtibial prosthetic device comprising a pylon configured as a unitary truss structure formed of a plurality of elongated supports interconnected at nodes and having open spaces between supports of the plurality of elongated supports. The unitary truss structure has a non-repeating geometry, and at least some of the supports of the plurality of elongated supports are oriented diagonally with respect to a central longitudinal axis of the pylon and curve three-dimensionally around the central longitudinal axis. A foot-ankle complex extends as a unitary single piece from a base of the pylon, the foot-ankle complex comprising an s-shaped posterior portion, an s-shaped anterior portion, and a sole portion. The s-shaped posterior portion and the s-shaped anterior portion both extend from the sole portion, have upper portions with curvatures that are concentric with each other, and are separated from each other by a gap. A terminal portion of the s-shaped anterior portion is near the base of the pylon and is unconnected to the base of the pylon.

DETAILED DESCRIPTION OF THE PREFERRED EMBODIMENTS

A preferred embodiment is a unibody transtibial prosthetic device. The preferred device provides an endoskeletal unibody design, bioinspired aspects, and foot design that provides a smooth, symmetrical gait and energy recapture using a purely passive structure and without sliding connections. Another preferred embodiment is a patient-specific design workflow. The workflow includes a series of digital scanning, design, and fabrication steps that enable lower cost, higher precision, better comfort, and a more robust prosthesis to be provided compared to conventional molding, sculpting, and assembly processes. A preferred embodiment is a 3D printed prosthetic limb with a custom fit socket fabricated from a digital model of the residual limb.

Preferred embodiments of the invention will now be discussed with respect to drawings and experiments. Broader aspects of the invention will be understood by artisans in view of the general knowledge in the art and the description of the experiments that follows.

Figure 1A:
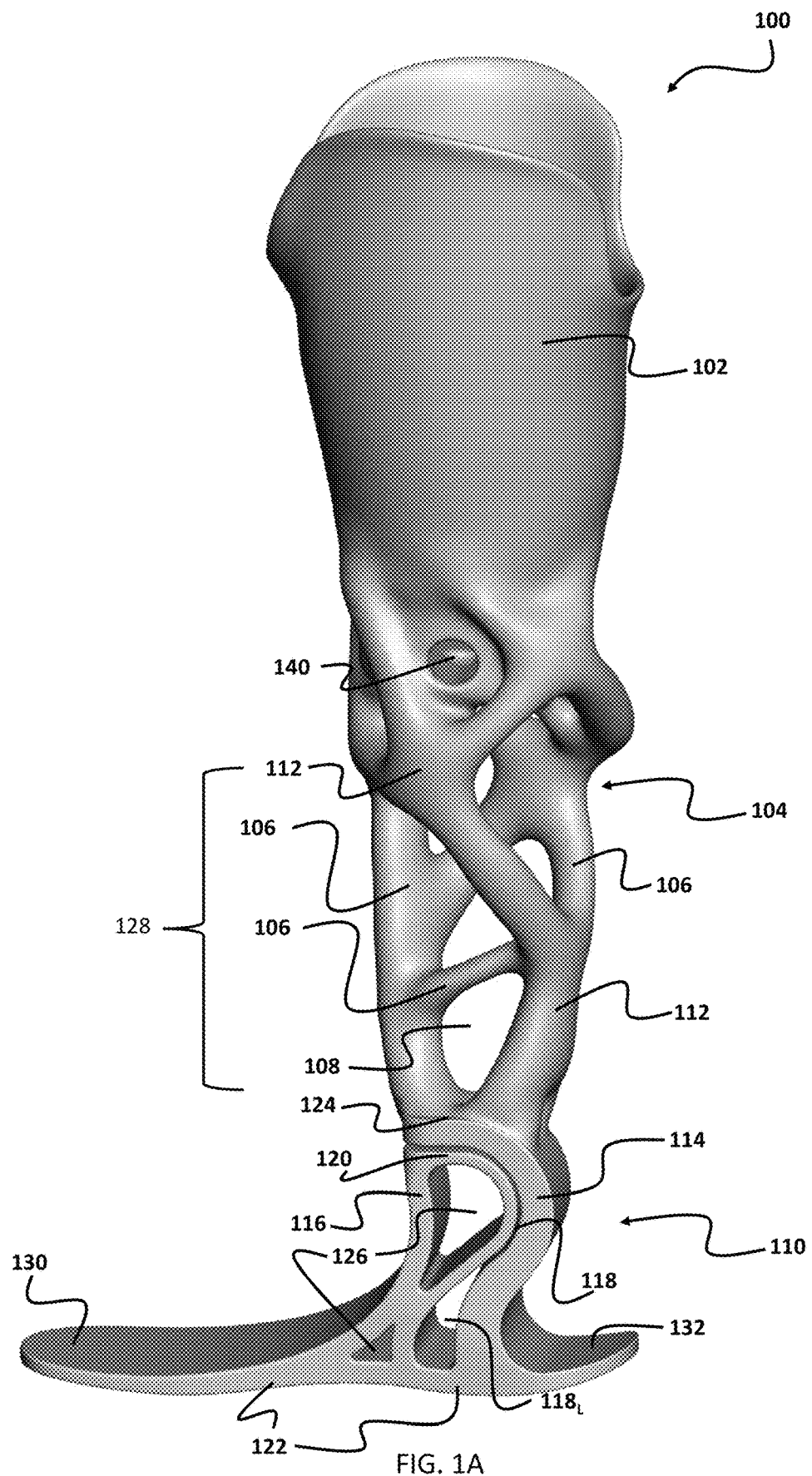
FIG. 1A is a perspective view of a preferred embodiment of a unibody transtibial prosthetic device.

FIG. 1A shows a preferred embodiment of a unibody transtibial prosthetic device 100. The prosthetic device 100 includes a socket 102 configured to attach to a residual limb. A pylon 104 extends from the socket 102. The pylon 104 is a unitary bioinspired truss structure of interconnected elongated supports 106 having open spaces 108 therebetween. It is preferably made from thermoplastic material. A foot-ankle complex 110 is a unitary polymer extending from the pylon 104. The foot-ankle unitary structure 110 is shaped to provide multi-axial dynamic flex to enable dorsiflexion, plantar flexion, inversion and eversion movement for smooth symmetric gait performance.

Figures 3A, 3B, 3C:
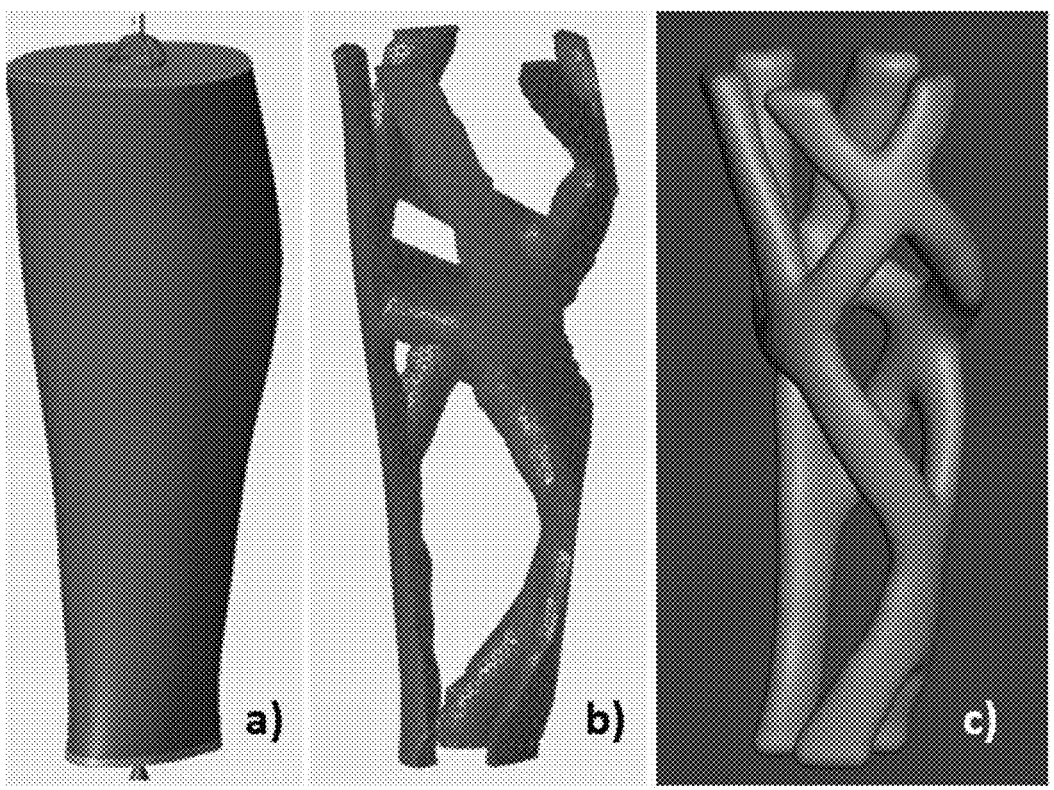
FIGS. 3A-3C illustrate respectively a 3D Scan of a tibial region of a contralateral healthy leg, topology optimization of pylon region and a smooth version of the optimized pylon.

It is preferred that the socket 102, pylon 104 and foot-ankle 110 structures are a unitary single piece. Single and multiple materials with different properties in different regions can be used to print a unitary single piece with tailored stiffnesses in different regions. Through the combination of 3D scanning and topology optimization, the pylon 104 can be shaped and dimensioned to be within extended external boundaries of the residual limb and can be very lightweight with the total amount of polymer material in the pylon 104 being minimized to achieve a given targeted K-level of use. Further, the truss structure formed by interconnected supports and nodes and blended with the ankle-foot complex provides a dynamic, multiaxial response during the gait cycle with energy capture and release achieved through the entire shin-ankle-foot. The optimization process for the pylon 104 includes the example discussed below with respect to FIGS. 3A-3C.

The entire prosthesis can be very lightweight but still be for a K-level 2 through K-level 4. As seen in FIG. 1, the interconnected elongated supports 106 have connection node portions ("nodes") 112 and define a central open cavity and curve around the open cavity. That is, the interconnected elongated supports 106 gently curve or arc into the nodes 112 and a cavity exists between the interconnected elongated supports 106 along a central longitudinal axis of the pylon 104. The central open cavity has a decreasing diameter from the socket 102 to the foot-ankle complex 110 in a manner resembling the decreasing size of a human transtibial leg portion. An outer imaginary boundary of the interconnected elongated supports and nodes 112 follows the mirrored shape of the contralateral transtibial leg portion of a patient. With imaging and 3D printing methods of making discussed below, the mirrored model is based upon the 3D scan data from the contralateral transtibial leg portion of a patient, if available. If not available, then another embodiment is a pylon structure that uses starting geometry of a transtibial leg portion from a database. The database model can be selected based on weight, activity level and aesthetics, among other things, and will be scaled to appropriately fit the specific patient. Generally, the interconnected elongated supports 106 and open spaces 108 can define a bioinspired truss structure with an outer boundary that follows the mirrored model of the sound contralateral leg of the patient.

The preferred material for the pylon 104 and for the entire prosthesis 100 is a 3D printable thermoplastic. With regard to the pylon 104, the thermoplastic material permits alignment adjustments in the heat zone 128 during a patient fitting, if necessary. In addition, the fit of the socket can be modified via thermoforming any specified region where pressure needs to be increased or decreased. However, a preferred embodiment is a prosthesis that is aligned properly during the design phase and does not require any modifications post-fabrication, and present methods provide a better chance of a patient specific prosthetic that can be used without any post-fabrication methods. While the leg can very closely model a missing leg of a patient, it will be the rare case where some adjustment is not needed. Advantageously, due to the endoskeletal design, by heating the pylon to a pliable temperature, adjustments can be made during a final fitting of a patient.

The foot-ankle complex 110 includes an s-shaped posterior portion 114 and s-shaped anterior portion 116 separated from each other by a gap 118 extending from a terminal portion 120 of the s-shaped anterior portion 116 to a sole portion 122. This defines a split ankle portion that gives a dynamic response with energy recapture. The gap is preferably small in its upper portion and widens to a teardrop profile shape in its lower portion 118L. An upper portion 124 of the posterior s-shaped portion 114 can be unitary with a lowest portion of the pylon 104, essentially forming a base of the pylon 104 with the pylon 104 and foot-ankle complex 110 forming a unitary single piece structure with each other and also with the socket 102. To handle more force through the pylon 104 and foot-ankle complex 110, the s-shaped posterior portion 114 can be solid and substantially thicker than the s-shaped anterior portion 116, which itself can include one or more pass-through openings 126. The sole portion 122 may include a split toe 130 and a split heel 132. The split toe and heel are useful for uneven terrain, where exaggerated inversion and eversion is beneficial. Overall, the unitary foot and pylon portions have no mechanical linkages, joints or sliding mechanisms, such as ball-socket connections or multi-link pinned connections, which will result in long-term durability.

The prosthesis can meet all requirements for government run health systems or insurance carriers. As an example, the United States Medicare program uses "L Codes, such as the following examples.

L5301—below knee, molded socket, shin, SACH foot, endoskeletal system (base code). The present prosthesis 100 meets this and L5637—addition to lower extremity, below knee, total contact socket has total contact surface against residual limb.

L5645—addition to lower extremity, below knee, flexible inner socket, external frame inner socket pockets that add flexibility and increase comfort, prominent bone projection can be met with tailored soft areas in the socket.

L5647—addition to lower extremity, below knee suction socket. The socket can include a one-way expulsion valve with a suspension sleeve to create a suction fit.

L5671—addition to lower extremity, below knee/above knee suspension locking mechanism (shuttle, lanyard or equal), excludes socket insert pin lock. Generally, the socket can be fabricated to work with any conventional attachment scheme, including suspensions.

L5940—addition, endoskeletal system, below knee, ultra-light material (titanium, carbon fiber or equal). The present pylon and foot/ankle structure can be very lightweight. The open endoskeleton style components minimize material used, and can also use very light weight. In addition, the use of a single unitary one piece design can eliminate metals used in conventional pylons and attachments between components.

L5910—addition, endoskeletal system, below knee, alignable system. As described below, preferred embodiment prosthesis can be adjusted via a thermoforming alignment process.

L5981—all lower extremity prostheses, flex-walk system or equal dynamic response integrated pylon foot. The present preferred unitary prosthesis meets this code.

Figure 1B:
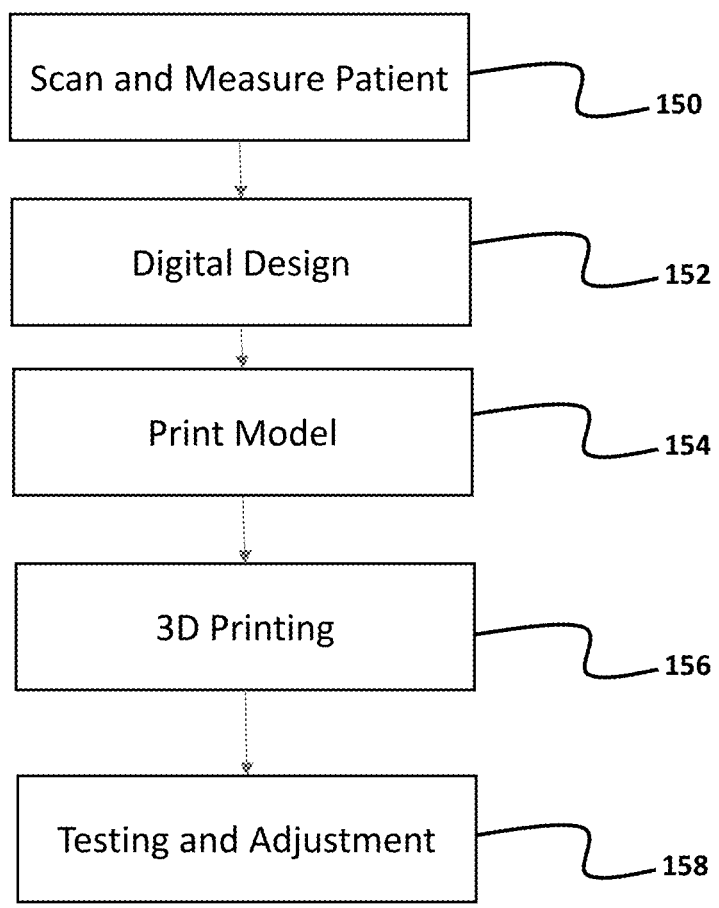
FIG. 1B is a flowchart of a preferred workflow for providing a custom fit unibody transtibial prosthetic device of FIG. 1A to a patient via imaging and 3D printing.

For a patient-specific fitting and fabrication method, a preferred method is illustrated in FIG. 1B. Patient image acquisition 150 can include photos, scan data or both, with the purpose of creating a digital twin of the patient. Photos can even be taken from a smart phone, which was demonstrated experimentally in the successful fabrication of a patient-specific prosthesis. A 3D model is next created 152 from the images and/or scan data. A preferred modelling is conducted from the photo data using structure from motion (SfM) techniques or with a structured light software (SL). For SfM, see C. Bregler, A. Hertzmann, and H. Biermann, "Recovering non-rigid 3d shape from image streams," Proceedings IEEE Conference on Computer Vision and Pattern Recognition. CVPR 2000 (Cat. No. PR00662); F. Dellaert, S. Seitz, C. Thorpe, and S. Thrun, "Structure from motion without correspondence," Proceedings IEEE Conference on Computer Vision and Pattern Recognition. CVPR 2000 (Cat. No. PR00662). For SL, J. Geng, "Structured-light 3d surface imaging: a tutorial," Advances in Optics and Photonics, vol. 3, no. 2, p. 128, 2011; S. Dunn, R. Keizer, and J. Yu, "Measuring the area and volume of the human body with structured light," IEEE Transactions on Systems, Man, and Cybernetics, vol. 19, no. 6, p. 1350-1364, 1989. In a preferred embodiment, a smartphone with a facial recognition camera, such as the Apple iphone XR TrueDepth Camera, is used to scan the patient using an app such as COMB. This enables a low-cost, highly mobile solution to produce a digital twin of the entire patient in STL format. In another embodiment, the facial recognition camera is used to capture only the regions of interest, such as amputated limb and foot and calf sections of their contralateral limb. In another embodiment a structured light scanner is used to scan either the entire patient or specific regions of interest necessary to design the unibody prosthetic limb. In another embodiment, a series of photographs are taken using any digital camera, such as the rear facing camera on any smartphone and reconstructed using the photogrammetry technique to create a point-cloud digital twin of the patient.

G-code for printing (print model) is generated 154 from the 3D model. This is accomplished via slicing software. Example settings used in experiments included a nozzle size 1.4 mm, layer height 0.7 mm, print speed 2000 mm per minute, nozzle temperature (varies by material between 240-280 degrees Celsius), bed temperature (varies by material between 90-140 degrees Celsius), chamber temperature (varies by material between 70-90 degrees Celsius), infill 100% density. These settings are used in the slicing software, regardless of which software is used. These settings control how the printer behaves during manufacturing. Artisans will recognize adjustments based upon materials being printed. The prosthetic is then printed via 3D printing 156, which can be printing remotely and shipping to a fit practitioner/patient or sending print data for printing near the fit practitioner/patient. This allows a patient to be imaged where they reside and also receive a prosthesis at that location. Testing and adjustment 158 includes the patient testing the prosthetic for fit and performance. A fitting practitioner can make minor adjustments to alignment and socket fit through thermoforming. In a preferred embodiment, a heat gun is used to raise the temperature of the heat zone 128 until it is pliable (above the material's glass transition temperature and below the material's melting temperature, checked using a handheld laser temperature gauge). In another embodiment, radiative heating is used to raise the temperature of the heat zone 128 until it is pliable. Other methods such as using a torch/flame may lead to difficulty controlling heat distribution but are still possible methods for heating the heat zone 128. Alignment should be controlled using an alignment jig that would clamp the ankle in place and allow for controlled rotation and translation in the sagittal, frontal, and transverse planes. Rotation should be controlled to less than one degree and translation precision to one millimeter. The socket is heated locally to adjust fit in a specific area where pressure may need to be relieved or increased against the patient's amputated limb. Adjustments to fit within the socket are achieved manually using a sturdy wooden bar with a rounded end that is pressed into the region of interest to increase or relieve pressure on the patient's amputated limb. As a note, thermoforming is a common practice in traditional prosthetic clinics as many check sockets, socket liners, etc. are thermoplastics. However, traditional prosthetic sockets often employ composite materials so fit cannot be adjusted. This gives us an advantage because we can easily modify our socket if a patient experiences discomfort either during initial fitting or during a follow up appointment during the device lifetime. The general design of the foot can be standard, i.e. have the S shaped posterior and anterior sections, the split design starting narrow and going to a teardrop shape. However, the actual dimensions of the foot are customized for every patient based on their weight, activity level, use-case, etc.

The FIG. 1B method permits very convenient service and business models. For example, a patient can receive a functional prosthetic without ever physically meeting with a traditional specialist. In areas where no skilled prosthetists are available, a non-specialized practitioner should be able to make minor adjustments to the printed limb via the thermoforming process. It is always preferred to have a licensed prosthetist do the fitting and walking test, but in many parts of the world this isn't feasible and a prosthesis of the invention provides a workable alternative in such situations.

In preferred fitting and fabrication methods of the invention, imaging of a patient can be conducted remotely, and the data can be sent to the designer and 3D printing facility. Image data of a contralateral limb and portions of a residual limb are used with a preferred method implemented in software to create an optimized patient-specific printed prosthesis in accordance with FIG. 1A. Additional preferred features of the method of FIG. 1B will be understood by artisans with reference to the following discussion of experiments that show imaging, printing, fitting and testing of prototype prostheses of the invention.

3D printing can be generally considered an additive fabrication process. Other additive processes can be used. Additive processes should be able to deposit thermoformable materials and preferably allow more than one material in a single deposition, e.g., material extrusion, powder bed fusion and material jetting techniques. Material extrusion is the preferred method. Fused filament fabrication (FFF) is a preferred material extrusion technique.

The prosthesis can be made from various materials, while a thermoplastic is preferred for adjustment. Typical polymers used for 3D printing are; ABS, PLA, PC, PETG, Nylon, PEI and PEEK. Generally, any material that can be deposited and solidified can be used to form a prosthesis by the present methods. Preferred materials include thermoplastic pellets, filaments, and resins, and may contain additives such as foaming agents, fibers, and particles. Relevant processing temperatures range from 200-500 degrees Celsius. The material must adhere to a previous layer with a sufficient bond strength and should be reformable through the application of heat. The selected material preferably exhibits high elongation and excellent interlayer bonding. High elongation means an ultimate elongation of greater than 150%. Excellent interlayer bonding means high interlayer bonding leading to a tensile strength perpendicular to layers no less than 60% of the tensile strength of the material.

Figure 7:
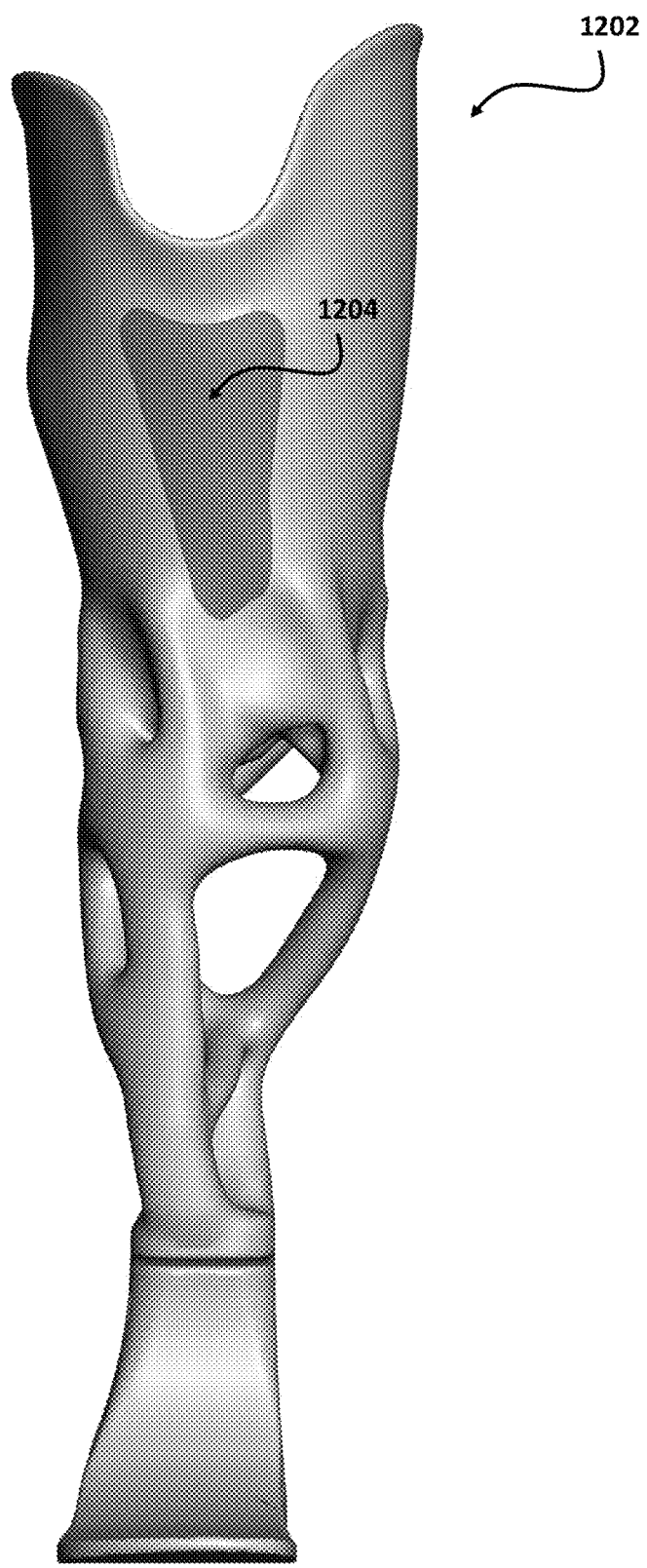
FIG. 7 illustrates a preferred multi-material unibody transtibial prosthetic device of the invention with a modified socket.

The 3D printing 156 can advantageously be multi-material printing to produce a unitary single-piece device. Use of multiple materials allows tailoring stiffness locally in the single print, which can improve gait performance, comfort, strength. For example, sensitive contact areas of the socket (see FIG. 7, area 1204) can be made softer than other regions to improve comfort. Another example includes a core-shell pattern where a 1-5 mm shell of the outer surface of the entire unibody (or any of the three portions) is flexible material and the core material is stiffer. Materials such as thermoplastic elastomers, thermoplastic urethanes, unfilled nylons and polypropylene, among others, would act as the flexible material, where materials such as chopped carbon or glass fiber filled nylons or polypropylenes, polycarbonate, PEEK, and PEI, among others, could act as the stiff material.

Experimental Data

Experiments demonstrated cost-effective 3D modeling of a patient's damaged limb through the use of smartphones and photogrammetry techniques. Some testing used separate components as a precursor to unitary single-piece transtibial prosthesis.

Patient Specific Workflow

A preferred workflow starts with a scan of amputee via the Comb scanner app (Comb O&P, Chardon, OH) which uses the facial-recognition camera in smartphones to generate 3D models of the patient. Scan data is supplemented by a patient measurement form and used to design a personalized prosthetic limb that follows the external shape of their mirrored contralateral limb. The digital design process for every device is done under the supervision of a certified prosthetist (CPO). The socket is created using scan data and patient measurements with prosthetic design software Neo (Rodin4D, Italy). The pylon with its present bioinspired truss structure is created using topology optimization software nTopology (nTopology, New York, NY) controlled to implement a pylon of the invention having a unitary bioinspired truss structure of interconnected elongated supports. The multi-axial dynamic foot-ankle complex is created in Fusion360 (Autodesk, San Rafael, CA) controlled to implement a foot-ankle complex of the invention that provides multi-axial dynamic flex. Finally, alignment and blending of the socket, pylon, and foot-ankle complex into the present unitary single-piece transtibial prosthesis is done in Meshmixer (Autodesk, San Rafael, CA). The finished model is sliced into G-code the 3D printer can interpret using Simplify3D (Simplify3D, Cincinnati, OH). The Fused filament fabrication (FFF) manufacturing process uses engineering grade thermoplastics to produce a strong and durable endoskeletal prosthetic device. The UniLeg is shipped to a prosthetist or physician who helps the amputee put on their personalized limb and confirms a smooth, symmetric gait. If any modifications are desired, thermoforming can be used to adjust fit and alignment.

Imaging and Modelling

Pervasively available smartphone imaging technology is useful to create 3D models of the patient. The Comb scanner app (Comb O&P, Chardon, OH) uses the front-facing facial-recognition camera available on many smartphones, e.g. the TrueDepth camera on iPhones (Apple, Cupertino, CA). Imaging can be performed on-site anywhere in the world and the scan data and measurement form are then sent to a fabricator (or a cloud operated by the fabricator). At a minimum, scans are taken of the amputee's residual limb and contralateral side.

Socket Design

Figure 2:
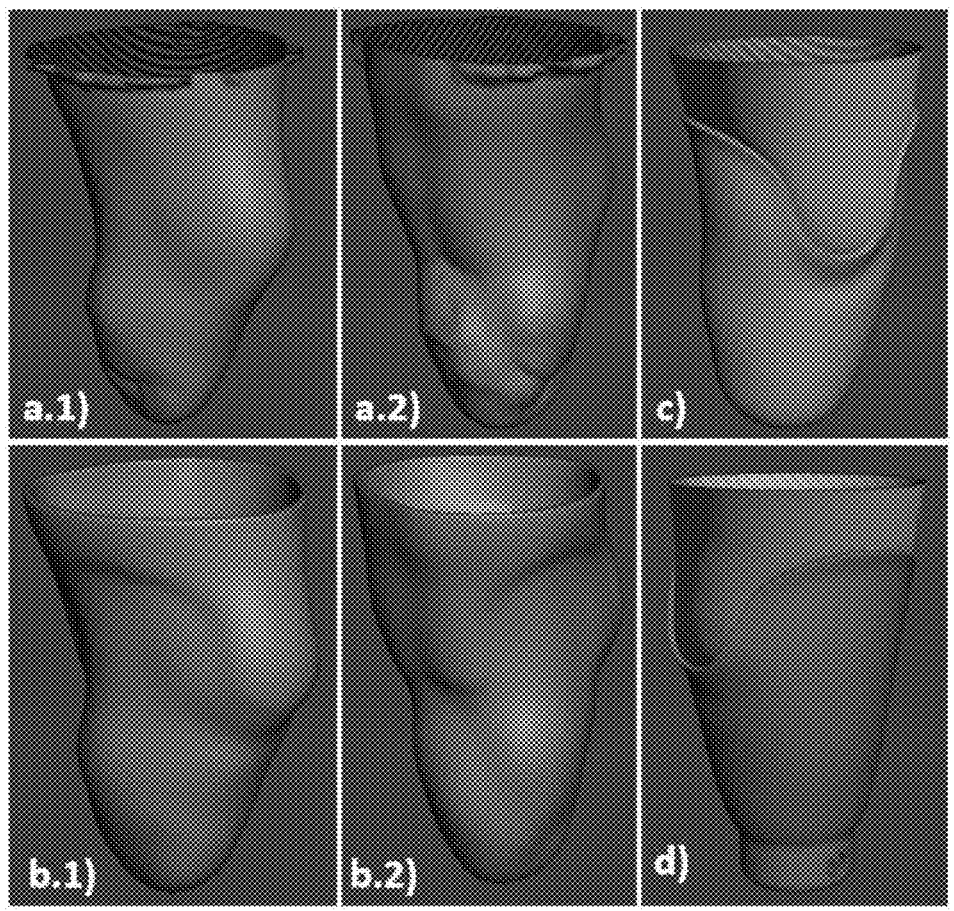
FIG. 2 shows a process for generation of a patient fit socket portion.

Scan data from the amputee's residual limb is used as the starting shape for the socket, in a process illustrated in FIG. 2. Modifications are made with Neo (Rodin4D, Italy) to properly distribute load and prevent pressure spots. The process is as follows: (1) the mesh is cleaned, smoothed, and the volume is reduced by 3% (a1,2); (2) a 2 cm wide by 1 cm deep slot is carved for the patellar tendon bar, which is a primary load-bearing feature, and the medial-lateral area is compressed by 2% (b1,2); (3) socket trim lines are delineated to allow proper knee mobility and the socket walls are thickened to 4 mm (c); (4) an extruded section at the distal end is created to house the shuttle-lock (d). Modification values can change from patient to patient, and this process can benefit from guidance by a CPO.

Pylon Design

A pylon of the invention is designed to be strong and 3D printable, while reducing material use to reduce cost and manufacturing time. The pylon is expected to withstand a series of compressive and torque loads based on patient weight and activity level and following ISO standard 10328. Topology optimization (TO) software nTopology (nTopology, New York, NY) is used to generate an optimal truss structure consistent to provide the unitary bioinspired truss structure of interconnected elongated supports having open spaces therebetween. The mirrored model of the transtibial section of the amputee's contralateral limb is used to generate the pylon. In cases where a bilateral amputee doesn't have a sound limb, a generic transtibial limb can be selected from a database and then reoriented and scaled to fit the patient. Model preparation for TO requires the definition of design space (FIG. 3A), where topology is optimized, and boundary condition regions (top and bottom disks in FIG.

3A), where loads and constraints are placed. Topology optimization is performed with the objective of maximizing stiffness.

The resultant mesh (FIG. 3B) was exported as an STL file and then imported into mesh modeling software Meshmixer (Autodesk, San Rafael, CA) to be smoothed and scaled to the correct dimensions. The final personalized bio-truss structure of the invention, FIG. 3C, has an outer contour that follows that of the mirrored contralateral limb of the specific amputee. A significant advantage of the endoskeletal truss structure is that it can deform without buckling, which enables adjustment of alignment by thermoforming.

Ankle-Foot Complex

Figures 4A, 4B, 4C:
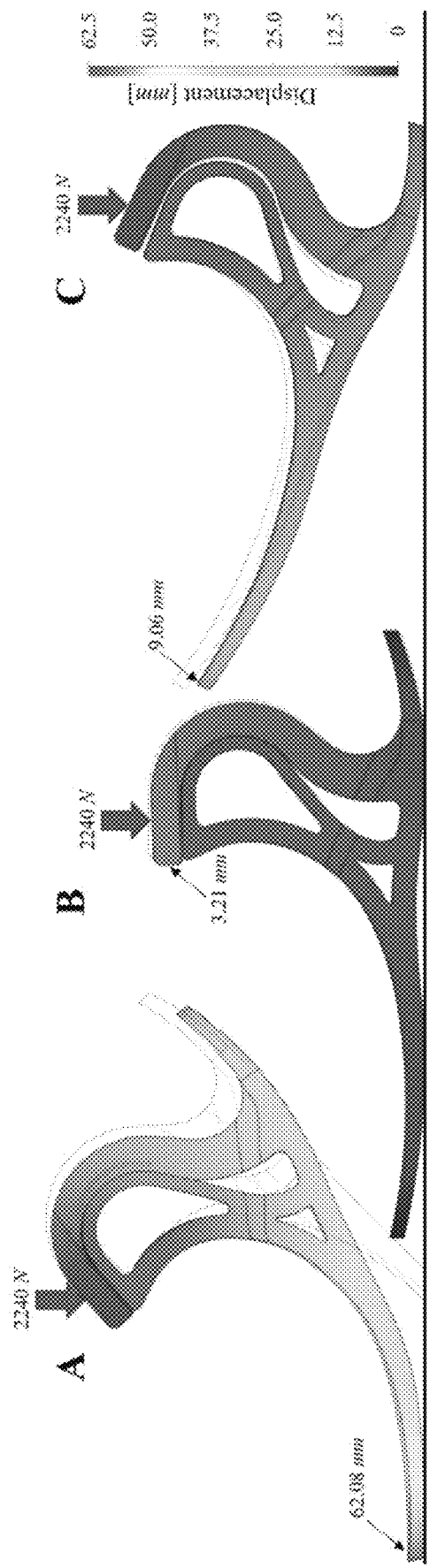
FIGS. 4A-4C illustrate respective forefoot, heel and u-axis loading conditions.

The foot-ankle complex is designed to provide a multi-axial dynamic response to enable dorsiflexion, plantar flexion, inversion and eversion motion for smooth symmetric gait performance and energy capture and return, which is illustrated in FIGS. 4A-4C. As discussed above, the foot-ankle complex includes s-shaped posterior and s-shaped anterior sections that are separated from each other by a gap. This defines a split ankle that enables plantar flexion during heel-strike, demonstrated in FIG. 4C. As the person transitions to mid-stance, FIG. 4B, the split ankle gap closes, providing stability. Transitioning to terminal stance, the entire foot-ankle complex coils to capture energy, FIG. 4A, which will be released to drive forward into the next gait cycle. The top of the ankle-foot complex is blended into the base of the pylon, which provides a smooth transfer of load from the ground through the dynamic pylon up to the socket. The sole portion may include a split toe and split heel. The split toe and heel are useful for uneven terrain, where exaggerated inversion and eversion is beneficial.

Digital Alignment and Integration

Figures 5A, 5B:
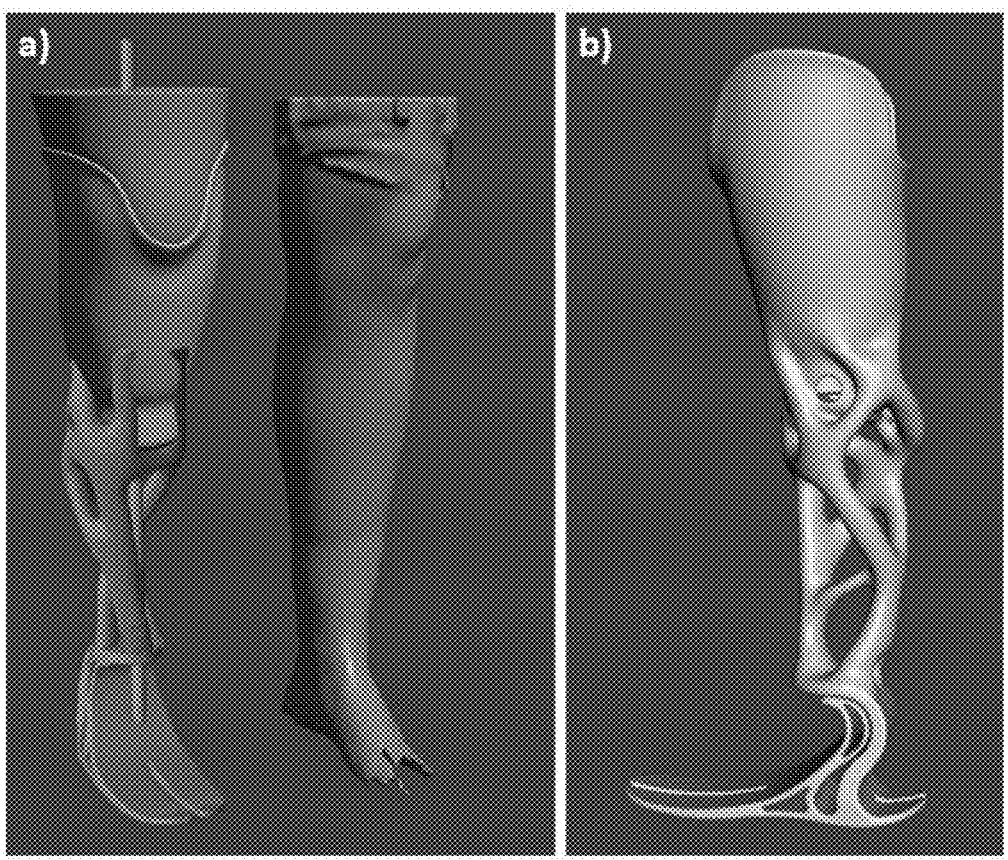
FIGS. 5A & 5B illustrate a process for the design of a unibody transtibial prosthetic device based upon a patient's contralateral healthy limb.

The socket, pylon, and foot-ankle complex are aligned and blended into the single-piece UniLeg in Meshmixer (Autodesk, San Rafael, CA), as illustrated FIGS. 5A and 5B. Alignment is guided using the mirrored model of the contralateral limb. A cylinder is drawn that runs through the middle of the mirrored leg to align the knee and ankle positions, FIG. 5A. The resulting unibody design, FIG. 5B, can be fully printed in one piece. The only commercial component used is a shuttle lock and pin system to secure the residual limb in the socket, such as into hole 140 of FIG. 1A. If necessary, an on-site prosthetist or physician can make minor adjustments to alignment and socket fit through thermoforming. A heat gun is used to raise the temperature of the pylon until it is pliable, which allows manual rotation and translation in the sagittal, frontal, and transverse planes. Adjustments to fit within the socket are achieved by heating the region of interest to pliability and then using a sturdy wooden bar with a rounded end that is pressed into the region of interest to increase or relieve pressure on the patient's residual limb.

Thermoforming is a common practice in traditional prosthetic clinics as many check sockets are thermoplastics. However, traditional prosthetic sockets often employ composite materials so fit cannot be adjusted. The inventive prosthesis provides a great advantage as it can be easily modified via thermoforming if a patient experiences discomfort either during initial fitting or during a follow up appointment during the device lifetime.

Validation with a Patient Fitting

A patient was fitted with a unibody transtibial prosthetic device of the invention. Alignment was assessed in anterior and lateral planes with the patient standing. For proper TKA alignment, the trochanter (hip), knee, and ankle points must fall along a vertical line when standing. To quantify the benefits of the present unibody transtibial prosthetic device, a comparison of weight, cost, and time of design were made against a patient's existing prosthetic device. Weight comparison between the devices revealed a 55% weight reduction from the conventional prosthetic, which weighed 4 pounds, to the present device weighing only 1.8 lbs. Lighter weight devices reduce metabolic cost during activity and are often reported to be more comfortable. Time of design and manufacture was compared between the two design methodologies. Total traditional transtibial prosthetic leg time for design and manufacture was estimated at 14 days. This estimate includes measurements (1 Day), mold creation (3 Days), socket creation (6 Days), and assembly and alignment (4 Days). In comparison, the present unibody design and manufacture time is 16 hours, which consists of data acquisition (1 Hour), design time (3 Hours), and printing time (12 Hours).

Modified Designs

Figure 6:
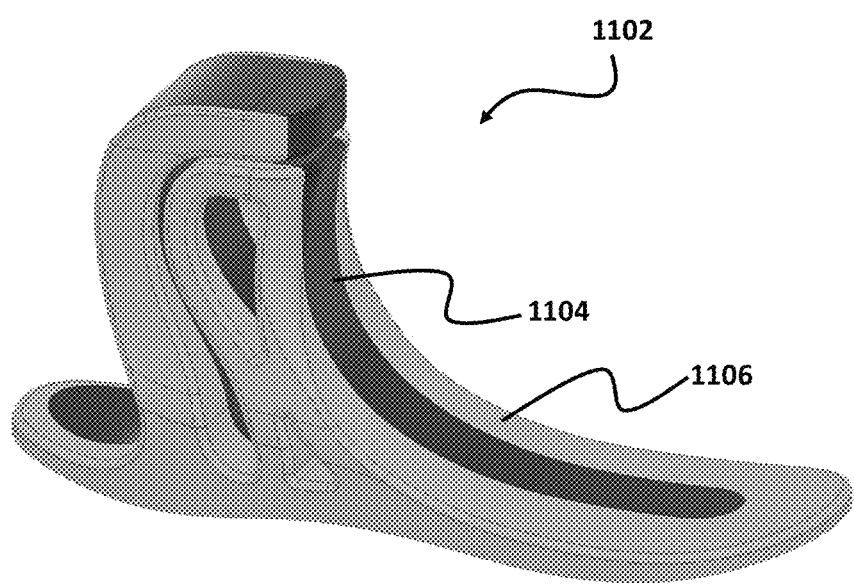
FIG. 6 illustrates a preferred multi-material foot/ankle complex of the invention.

FIG. 6 shows a preferred foot/ankle complex 1102 that is consistent with the general shape, arrangement, and structure of the foot/ankle complex 110 of FIG. 1A. The foot/ankle complex 1102 includes central strip 1104 of stiffer material surrounded by more flexible material 1106. The ratio of the two materials controls energy return, flexibility, and dynamic range. While not shown in FIG. 6, the foot/ankle complex 1102 is unitary with a pylon section and socket section.

FIG. 7 illustrates a unibody prosthetic 1202 of the invention that includes one or more (interior/patient contact side) pockets 1204 of flexible material of pressure sensitive areas of the patient's amputated limb. These areas can be identified by the patient or physician during visit to the clinic as scanning occurs.

Experiment Observations.

The demonstrated imaging and 3D printing workflow can be used to provide prosthetic devices to virtually any person cared by a practitioner that has a smart phone for imaging, which can benefit rural communities, where high-tech, medical imaging devices such as CT scanners are not available or cost-prohibitive. The workflow provides custom-fitted prostheses that are comfortable and high-performance.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A transtibial prosthetic device comprising:
   a pylon configured as a unitary truss structure formed of a plurality of elongated supports interconnected at nodes and having open spaces between supports of the plurality of elongated supports, the unitary truss structure comprising a polymer; and
   a foot-ankle complex extending from a base of the pylon, the foot-ankle complex comprising:
   a sole portion;
   an s-shaped posterior portion extending from a first location on the sole portion to the base of the pylon; and
   an s-shaped anterior portion extending from a second location on the sole portion to a terminal portion of the s-shaped anterior portion near the base of the pylon, the terminal portion being unconnected to the base of the pylon;

wherein the s-shaped posterior portion and the s-shaped anterior portion are separated from each other by a gap that extends from the terminal portion to the sole portion.

2. The transtibial prosthetic device of claim 1, wherein near the terminal portion of the s-shaped anterior portion, the gap runs transverse to a central longitudinal axis of the pylon and along the base of the pylon.

3. The transtibial prosthetic device of claim 1, wherein the terminal portion of the s-shaped anterior portion is directly below an anterior end of the base.

4. The transtibial prosthetic device of claim 1, wherein the gap widens to a teardrop shape in a lower portion of the gap near the sole portion.

5. The transtibial prosthetic device of claim 1, wherein the gap is located within a volume below the base of the pylon, the volume having a cross-sectional area of the base of the pylon.

6. The transtibial prosthetic device of claim 1, wherein an upper portion of the s-shaped posterior portion and an upper portion of the s-shaped anterior portion have curvatures that are concentric with each other.

7. The transtibial prosthetic device of claim 1, wherein the s-shaped posterior portion is solid and thicker than the s-shaped anterior portion, and the s-shaped anterior portion includes a pass-through opening.

8. The transtibial prosthetic device of claim 1, wherein:
the unitary truss structure has a non-repeating geometry; and
at least some of the supports of the plurality of elongated supports are oriented diagonally with respect to a central longitudinal axis of the pylon and curve three-dimensionally around the central longitudinal axis.

9. The transtibial prosthetic device of claim 1, wherein at least some of the supports curve into the nodes, define a central open cavity, and curve around the central open cavity.

10. The transtibial prosthetic device of claim 1, wherein the unitary truss structure is an endoskeletal design in which the polymer is a thermoplastic material, and the unitary truss structure is configured to enable adjustment of alignment by thermoforming.

11. The transtibial prosthetic device of claim 1, wherein the foot-ankle complex has an upper portion that is unitary with a lowest portion of the pylon, to form the base of the pylon.

12. The transtibial prosthetic device of claim 1, wherein the pylon or the foot-ankle complex comprises multiple materials with different stiffnesses.

13. A method of manufacturing the transtibial prosthetic device of claim 1, comprising printing the pylon and the foot-ankle complex as a unitary single piece using 3D printing.

14. A transtibial prosthetic device comprising:
a pylon configured as a unitary truss structure formed of a plurality of elongated supports interconnected at nodes and having open spaces between supports of the plurality of elongated supports, wherein the unitary truss structure has a non-repeating geometry, and at least some of the supports of the plurality of elongated supports are oriented diagonally with respect to a central longitudinal axis of the pylon and curve three-dimensionally around the central longitudinal axis; and
a foot-ankle complex extending as a unitary single piece from a base of the pylon, the foot-ankle complex comprising an s-shaped posterior portion, an s-shaped anterior portion, and a sole portion;
wherein the s-shaped posterior portion and the s-shaped anterior portion both extend from the sole portion, have upper portions with curvatures that are concentric with each other, and are separated from each other by a gap; and
wherein a terminal portion of the s-shaped anterior portion is near the base of the pylon and is unconnected to the base of the pylon.

15. The transtibial prosthetic device of claim 14, wherein the s-shaped posterior portion extends from a first location on the sole portion, and the s-shaped anterior portion extends from a second location on the sole portion, the second location being anterior to the first location.

16. The transtibial prosthetic device of claim 14, wherein the gap extends from the terminal portion to the sole portion and is located directly below the base of the pylon.

17. The transtibial prosthetic device of claim 14, wherein near the terminal portion of the s-shaped anterior portion, the gap runs transverse to the central longitudinal axis of the pylon and along the base of the pylon.

18. The transtibial prosthetic device of claim 14, wherein the terminal portion of the s-shaped anterior portion is directly below an anterior end of the base.

19. The transtibial prosthetic device of claim 14, wherein the pylon is fabricated from a thermoformable material.

20. The transtibial prosthetic device of claim 14, wherein the pylon or the foot-ankle complex comprises multiple materials with different stiffnesses.

* * * * *